(12) United States Patent
Zhao et al.

(10) Patent No.: US 8,822,194 B2
(45) Date of Patent: Sep. 2, 2014

(54) CANCER SELECTIVE AUXOTROPHS

(75) Inventors: Ming Zhao, San Diego, CA (US); Meng Yang, San Diego, CA (US)

(73) Assignee: Anticancer, Inc., San Diego, CA (US)

( * ) Notice: Subject to any disclaimer, the term of this patent is extended or adjusted under 35 U.S.C. 154(b) by 2149 days.

(21) Appl. No.: 11/631,247

(22) PCT Filed: Jun. 29, 2005

(86) PCT No.: PCT/US2005/023454
§ 371 (c)(1),
(2), (4) Date: Apr. 13, 2009

(87) PCT Pub. No.: WO2006/004992
PCT Pub. Date: Jan. 12, 2006

(65) Prior Publication Data
US 2009/0300779 A1   Dec. 3, 2009

Related U.S. Application Data

(60) Provisional application No. 60/584,301, filed on Jun. 29, 2004.

(51) Int. Cl.
*C12N 1/21* (2006.01)
*A61K 38/20* (2006.01)
*A61K 35/74* (2006.01)
*A61K 38/51* (2006.01)

(52) U.S. Cl.
CPC ............ *A61K 35/74* (2013.01); *A61K 38/2013* (2013.01); *A61K 38/51* (2013.01)
USPC .................................................. 435/252.3

(58) Field of Classification Search
None
See application file for complete search history.

(56) References Cited

U.S. PATENT DOCUMENTS 6,524,571 B1 * 2/2003 Xu et al. ...................... 424/93.2
2003/0161788 A1   8/2003 Zhao et al.

FOREIGN PATENT DOCUMENTS

| WO | WO-96/40238 | 12/1996 |
| WO | WO-03/006069 | 1/2003 |
| WO | WO-03/057007 | 7/2003 |

OTHER PUBLICATIONS

Supplementary European Search Report for EP 05763615.1, mailed Jul. 9, 2008, 2 pages.
Dang et al., PNAS USA (2001) 98:15155-15160.
Hoiseth et al., Nature (1981) 291:238-239.
International Search Report for PCT/US2005/023454, mailed on Nov. 29, 2005, 1 page.
Low et al., Nature Biotech. (1999) 17:37-41.
Nature Biotechnology (2005) 23:189.
Pawelek et al., Cancer Res. (1997) 57:4537-4544.
Toso et al., J. Clin. Oncol. (2002) 20:142-152.
Yazawa et al., Breat Canc. Res. and Treat. (2001) 66:165-170.
Yu et al., Nat. Biotechnol. (2004) 22:313-320.
Zhao et al., PNAS USA (2005) 102:755-760.
Zhao et al., Proc. Am. Assoc. Cancer Res. (2004) 45:869 (No. 3765).

* cited by examiner

*Primary Examiner* — Richard Hutson

(57) ABSTRACT

Bacteria that are auxotrophic for at least two amino acids found in at least one tumor are effective anti tumor treatments, labeling agents, and vaccines against infection. Improved antitumor effects can also be provided such strains by passage through an appropriate tumor model.

9 Claims, 5 Drawing Sheets

Virulence of *S. typhimurium* A1 mutant in PC-3 human prostate tumor cells

Toxicity of *S. typhimurium A1* compared to wild type in non-tumor bearing nude mice.

Effect of *S. typhimurium* A1 on growth of PC-3 human prostate cancer in nude mice after IV injection.

US 8,822,194 B2

CANCER SELECTIVE AUXOTROPHS

CROSS-REFERENCE TO RELATED APPLICATIONS

This Application is a U.S. National Phase of PCT/US2005/023454, filed 29 Jun. 2005, which claims priority to U.S. Provisional Application Ser. No. 60/584,301, filed 29 Jun. 2004. The contents of these applications are incorporated herein by reference.

TECHNICAL FIELD

The invention relates to antitumor bacteria that have been modified to require at least two amino acids as nutrients, and may further show increased adherence and virulence to tumors. As an illustration, *Salmonella typhimurium*, which comprises a double auxotrophic mutation to require arginine and leucine is demonstrated to be non-toxic in vivo and selective for growth in tumors.

BACKGROUND ART

It is well known that anaerobic bacteria grow selectively in tumors, and indeed, bacteria in large numbers have been found in tumors excised from patients. In view of this, bacteria have been proposed as tumor therapeutics. For example, Yazawa, K., et al., *Breast Canc. Res. and Treat.* (2001) 66:165-170 demonstrated that *Bifidobacterium longum*, a non-pathogenic Gram-position bacterium, when injected intravenously, grew selectively in mammary tumors induced in rats. Dang, L. H., et al., *Proc. Natl. Acad. Sci. USA* (2001) 98:15155-15160 demonstrated that a strain of *Clostridium novyi* which had been depleted of its lethal toxin produced spores that germinated within avascular regions of tumors in mice and destroyed surrounding viable tumor cells.

*Salmonella typhimurium*, which are auxotrophic by virtue of disruption of the aro gene, were shown to have suppressed virulence and thus useful as live vaccines as described by Hoiseth, S. K. J., et al., *Nature* (1981) 291:238-239. The disruption of the aro gene blocked the production of both para-aminobenzoic acid (PABA) and of 2,3-dihydroxybenzoate (DHB). Earlier work that resulted in *Salmonella* auxotrophic only for PABA, and *Salmonella* auxotrophic only for DHB also resulted in reduced virulence, but disruption of the aro gene, resulting in the double auxotroph were characterized as virtually non-virulent. Pawelek, J., et al., *Cancer Res.* (1997) 57:4537-4544 describe *Salmonella* mutants that were pur (requiring adenine and vitamin B1) as antitumor therapeutics with reduced pathogenicity. Low, B., et al., *Nature Biotech.* (1999) 17:37-41 reported lipid-A-mutant *Salmonella* with disruption in the msbB gene which reduced TNFα induction and increased $LD_{50}$ by 10,000-fold. Tumor accumulation ratios in excess of 1,000:1 compared with normal tissues were reported. Melanomas in mice treated with these modified *Salmonella* were 6% of the size of tumors in untreated controls.

Further, an attenuated *S. typhimurium* has been evaluated in a Phase I clinical trial, as reported in Toso, J. F., et al., *J. Clin. Oncol.* (2002 20:142-152. Twenty-four patients with metastatic melanoma and one patient with metastatic renal cell carcinoma received IV bolus infusions containing $10^6$ to $10^9$ cfu/m² of the lipid-A-mutant *Salmonella typhimurium* (VNP20009) that was attenuated by deletion of both the purI and msbB genes. The purI mutant requires an external source of adenine, and the msbB mutant prevents the addition of a terminal myristyl group to the lipid-A domain. The VNP20009 strain could be safely administered to patients, and at the highest tolerated dose, tumor colonization was observed.

The precision of bacterial treatment of tumors could, of course, be enhanced by systems for tracking the progress of bacterial infection. One such system is described in U.S. patent publication 2003-0161788, published 28 Aug. 2003 and incorporated herein by reference. As described in this publication, bacteria such as *E. coli*, labeled with fluorescent proteins are used to monitor infection and to evaluate treatments. In model systems, and indeed, in treated subjects, in addition to direct observation of the labeled bacteria per se, tumor tissue may be provided with a fluorescent label of a different color to provide a desirable contrast. In the exemplified embodiments, *S. typhimurium* modified to express a variant of the *A. victoria* green fluorescent protein (GFP) were injected into tumors labeled with red fluorescent proteins (RFP's) in nude mice. In alternative embodiments, *E. coli* modified to express RFP were injected into nude mice containing tumors labeled with GFP. It was noted that in addition to their own inherent antitumor affects, the bacteria also might be modified to produce a therapeutic, such as IL2 or methioninase.

Yu, Y. A., et al., *Nat. Biotechnol.* (2004) 22:313-320 have shown that bacteria, expressing GFP, injected intravenously into live animals replicate in solid tumors and metastases including tumors of the breast, prostate, brain and fibrosarcoma. Growth in tumors was imaged in real time using luciferase-catalyzed luminescence as well as GFP. *E. coli* and three attenuated pathogens, *Vibrio cholerae, S. typhimurium*, and *Listeria monocytogenes*, replicated in tumors.

There remains a need for improved bacterial strains with enhanced selectivity for tumors and reduced toxicity such that these improved strains may be used as therapeutics, vaccines, and as guides to monitoring tumor progression and evaluating and optimizing tumor treatment. The present invention provides such improved strains of bacteria. An abstract describing the effects of *S. typhimurium*, prepared in accordance with the invention, but not describing the nature of the mutations, was published by Zhao, M., et al., *Proc. Am. Assoc. Cancer Res.* (2004) 45:869 (No. 3765).

Detailed description of the auxotrophic strain A1 described hereinbelow is set forth in Zhao, M., et al., *Proc. Natl. Acad. Sci. USA* (2005) 102:755-760, incorporated herein by reference. A short summary appears in *Nature Biotechnology* (2005) 23:189.

DISCLOSURE OF THE INVENTION

The invention provides bacterial strains useful for the purposes set forth above that are auxotrophic for at least two amino acids, e.g., arginine and leucine. These double auxotrophs have greatly enhanced tumor selectivity, reduced toxicity and reduced production of TNFα when administered to subjects.

Thus, in one aspect, the invention is directed to an anaerobe or a facultative anaerobe modified to require at least two amino acids in its nutrient medium prepared as a pharmaceutical composition. In one embodiment, the double auxotroph of the invention is further modified to express a fluorescent protein.

In another aspect, the invention is directed to anaerobes as described in the previous paragraph with increased adherence, virulence and/or invasiveness which are obtainable by passage through an in vivo murine tumor model.

In other aspects, the invention resides in methods to treat tumors in subjects using the double (or more than double)

auxotrophs of the invention, and to vaccines which employ them. In still other aspects, the invention is directed to methods to monitor treatment by observing the behavior of the auxotrophs modified to contain a fluorescent protein when these bacteria are administered to, for example, tumor-bearing subjects. In one embodiment, the tumors themselves are labeled with fluorescent protein.

MODES OF CARRYING OUT THE INVENTION

Figure 1:
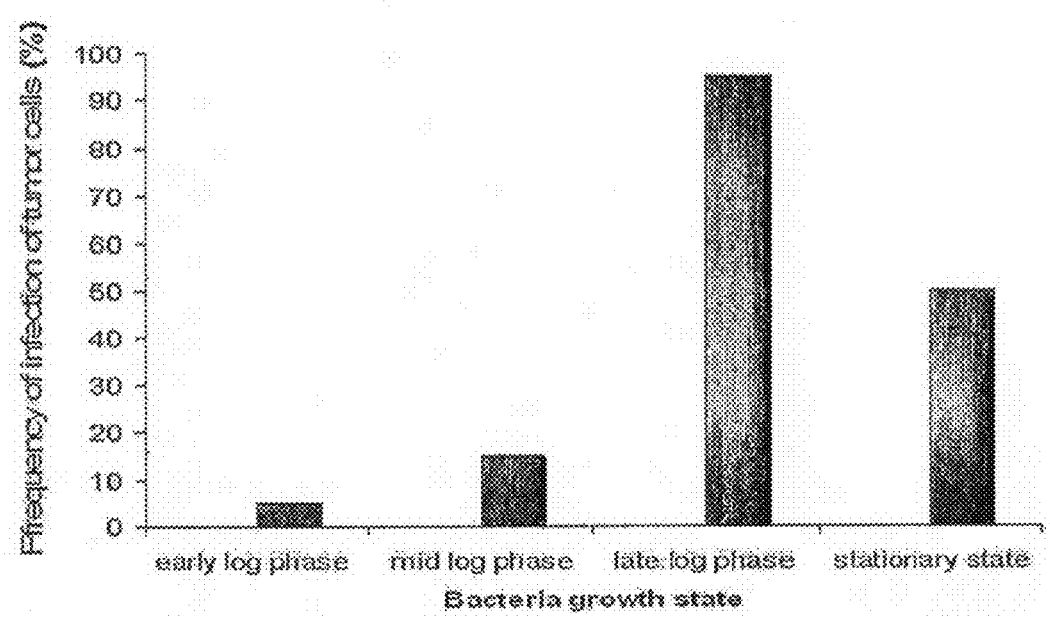
FIG. 1 is a graph showing the dependence of the virulence of *S. typhimurium* A1 mutant in PC-3 human prostate tumor cells as a function of its phase of growth.

Mutants of bacteria which are anaerobic or which are facultative anaerobes requiring at least two amino acids for growth are prepared using standard mutagenesis techniques. Where the genomic composition of the bacterium is known, as is in the case for *E. coli*, directed mutation or homologous recombination techniques, for example, could be used to effect these mutations specifically. Alternatively, non-specific mutation techniques using radiation or chemical stimulation can be employed followed by selection procedures which are standard in the art. For example, the mutagenized bacteria are grown on media which contain all required amino acids and individual colonies isolated. Those colonies which fail to grow on media lacking one of each amino acid are then picked and evaluated for growth on appropriate replacement media. Those colonies that require addition of at least two amino acids to the medium are chosen.

It has also been found that the double mutants, when passaged in an in vivo tumor model and re-isolated, yield colonies that have enhanced adherence and/or invasiveness and/or virulence with respect to tumor cells. These further modified bacteria are especially useful and non-toxic in the methods described for the auxotrophs hereinbelow.

Suitable anaerobic bacteria which can be modified in this way include the various strains of *Salmonella, Clostridium, Escherichia, Vibrio, Listeria, Bifidobacterium*, and any other convenient anaerobe.

In some cases, as, for example, *Clostridium*, further modification to detoxify the organism may also be required. The auxotrophs of the invention are useful in a variety of contexts, including direct therapy directed against tumors, vaccines against infection by the wildtype bacteria, carriers of expression systems for therapeutic proteins delivered to the tumors selectively, monitoring disease progression and evaluating candidate therapeutic protocols, as well as optimizing the protocols themselves. The characteristic feature of the invention bacteria is their dependence on at least two amino acids that are adequately supplied by the tumor and not by the host generally. Used for illustration hereinbelow is a double auxotroph requiring both leucine and arginine; however, other combinations, preferably of dissimilar amino acids, can also be used. Thus, mutants that require both histidine and methionine, both valine and aspartic acid, both glutamic acid and serine, and the like may also be employed. Preferably, the two amino acids required come from different pathways; thus, a combination of requirements for tryptophan and alanine, or glutamine and lysine, and the like can be employed. Preferred combinations are of a basic amino acid and a neutral amino acid, such as histidine/alanine; histidine/valine; histidine/leucine; arginine/leucine; arginine/valine; arginine/isoleucine; lysine/methionine; lysine/valine; and the like. Illustrated below is the combination of arginine and leucine auxotrophy.

This particular auxotroph is demonstrated below to be highly selective for growth in tumors and is non-toxic. Using studies on tumor cell lines, applicants have shown that after infection, the accumulation of large numbers of intracellular bacteria cause nonspecific destruction of mouse MMT breast cancer cells and mouse B16F10 melanoma cells. These double auxotrophs induced apoptosis and necrosis in PC-3 human prostate tumor cells. In vivo studies showed this mutant to be successful in treating PC-3 tumors and increasing survival time in afflicted mice.

As the auxotrophs of the invention must proliferate in tumor tissue, the amino acid requirements must be met by concentrations of these present in the tumor. Thus, the amino acids for which the bacteria are auxotrophic must be present at sufficient concentration to support growth. These must be present in at least one tumor type. Determination can readily be made in vitro using tumor cell cultures. Panels of said cultures are available from a variety of sources, such as the National Cancer Institute. As long as the cells grow in at least one cell culture, they fall within the scope of the invention.

Especially useful auxotrophs of the invention include those that show enhanced capacity to inhibit tumor growth, provide for tumor regression, and increase survival time either in therapeutic subjects or in laboratory research animals. These strains show enhanced adhesion and/or invasiveness and/or virulence with respect to tumors and are obtainable by in vivo passaging of the auxotrophs described above or of an anaerobic or facultative anaerobic in general through an in vivo tumor model. The tumor model for passaging is typically that related to an organ that is particularly favorable for the proliferation of the bacteria chosen. For example, as *S. typhimurium* typically inhabits the colon, it is preferred that a colon tumor model be employed. The mechanism by which the enhanced desirable properties is acquired is unclear, but such improved qualities can reliably be obtained as outlined in detail in the examples below by injecting the subject bacteria into the tumor model, recovering the bacteria from the tumor, for example, by homogenizing and recovering the supernatant, and selecting colonies for the desired properties.

The animal subjects which benefit from the therapeutic and prophylactic methods of the invention are of a full range of animals that are affected by solid tumors, but are typically vertebrates such as fish, birds and mammals, most typically mammals. The treatment of humans is of particular interest, but treatment of livestock, such as pigs, cows, sheep and goats, chickens, turkeys and the like is also clearly beneficial as is the treatment of companion animals such as dogs and cats. The methods of the invention provide real time observations without invasive techniques for any of these animal subjects due to the intensity of fluorescence emitted by the fluorescent proteins employed.

Also critically important is the use of laboratory animals, e.g., rats, mice and rabbits as model systems for disease progression and drug efficacy testing. Those embodiments of the invention that employ fluorescent bacteria are particularly useful in this context. However, disease progression in treated vertebrates can also employ labeled bacteria.

The auxotrophic anaerobes of the invention may be formulated into pharmaceutical and veterinary compositions useful as therapeutics and prophylactics. These compositions contain additional physiologically acceptable excipients; formulations for therapeutics and vaccines suitable for various routes of administration are found, for example, in *Remington's Pharmaceutical Sciences*, latest edition, Mack Publishing Co., Easton, Pa., incorporated herein by reference. The formulations may be in the form of powders, capsules, syrups, tablets, solutions for injection, and the like. Formulations for controlled release, liposomal formulations, and implants may be used. Choice of formulation and route of administration is dependent on the particular application and within ordinary skill.

When used to label tumors, for example, for monitoring progress of infection, fluorescent proteins are employed for labeling. Advantage is taken of visible marker fluorescent proteins to label the bacteria so that their migration and colonization in solid tumors can be followed and so that localized production of therapeutic agents by these bacteria can be controlled and evaluated.

Since sufficient intensity can be achieved by the use of fluorescent proteins to observe the migration of fluorescent cells and production of protein in the intact animal, in addition to determining these aspects, the progress of tumor regression and metastasis or suppression thereof can be observed in the intact subject in real time. This can be optimized by labeling the tumor cells themselves with a protein that fluoresces at a different wavelength.

The label used in the various aspects of the invention is a fluorescent protein, i.e., a protein that emits visible light when irradiated with an appropriate wavelength. The native gene encoding the seminal protein in this class, GFP has been cloned from the bioluminescent jellyfish *Aequorea victoria* (Morin, J., et al., *J. Cell. Physiol* (1972) 77:313-318). The availability of the gene has made it possible to use GFP as a marker for gene expression. The original GFP itself is a 283 amino acid protein with a molecular weight of 27 kD. It requires no additional proteins from its native source nor does it require substrates or cofactors available only in its native source in order to fluoresce. (Prasher, D. C., et al., *Gene* (1992) 111:229-233; Yang, F., et al., *Nature Biotechnol.* (1996) 14:1252-1256; Cody, C. W., et al., *Biochemistry* (1993) 32:1212-1218.) Mutation of the original GFP gene has been found useful to enhance expression and to modify excitation and fluorescence of the product, so that "GFP" in various colors, including reds, yellows and blues has been obtained. GFP-S65T (wherein serine at 65 is replaced with threonine) is particularly useful in the present invention method and has a single excitation peak at 490 nm. (Heim, R., et al., *Nature* (1995) 373:663-664); U.S. Pat. No. 5,625,048. Other mutants have also been disclosed by Delagrade, S., et al., *Biotechnology* (1995) 13:151-154; Cormack, B., et al., *Gene* (1996) 173:33-38 and Cramer, A., et al., *Nature Biotechnol.* (1996) 14:315-319. Additional mutants are also disclosed in U.S. Pat. No. 5,625,048.

By suitable modification, the spectrum of light emitted by the GFP can be altered. Thus, although the term "GFP" is often used in the present application because of historical custom, the proteins included within this definition are not necessarily green in appearance, and should simply be referred to as fluorescent proteins. Various forms of "GFP" exhibit colors other than green and these, too, are included within the usage of "GFP" and are useful in the methods and materials of the invention. In addition, it is noted that green fluorescent proteins falling within the definition of "GFP" herein have been isolated from other organisms, such as the sea pansy, *Renilla reniformis*. Any suitable and convenient form of "GFP" of any color can be used to modify the infectious agents useful in the invention, both native and mutated forms.

In order to avoid confusion, the simple term "fluorescent protein" will often also be used; in general, this is understood to refer to the fluorescent proteins which are produced by various organisms, such as *Renilla* and *Aequorea* as well as modified forms of these native fluorescent proteins which may fluoresce in various visible colors. In general, the terms "fluorescent protein" and "GFP" are sometimes used interchangeably; however, sometimes specific other colors can be noted. The system is strictly mnemonic so that, for example, RFP refers to red fluorescent protein, YFP to yellow fluorescent protein, BFP to blue fluorescent protein, etc. A wide range of wavelength of visible light is emitted by these proteins depending on the specific modifications made.

Because fluorescent proteins are available in a variety of colors, imaging with respect to more than a single color can be done simultaneously. For example, two different bacterial agents or three different bacteria each expressing a characteristic fluorescence can be administered to the subject or a single bacterium could be labeled constitutively with a single color and a different color used to produce a fusion with a gene product. The nucleotide sequence encoding a fluorescent protein having a color different from that used to label the bacterium per se can be inserted at a genetic locus of a protein to be produced or as a fusion protein in a vector with a therapeutic protein to be produced.

The multiplicity of colors is particularly advantageous in the context of the invention. For example, the tumor itself may be labeled with a fluorescent protein of one color, the bacterium administered labeled with a structural or intracellular protein of a different color so that the location of the bacterium can be better ascertained, and a protein product of the bacterium labeled with still a third color so that the level of production of this protein can be monitored. Thus, using whole body observation of a live animal, the location of the administered bacterium can be determined, the level of production of a therapeutic protein by that bacterium monitored, and the effect on the tumor monitored, all simultaneously.

The fluorescent proteins used in the present invention are of sufficient intensity that real time observation of the above phenomena in a living animal can be employed. This offers a major advance to the "blind" approach to bacterial delivery described in the prior art. Because the animal is alive, modifications to the treatment protocol to enhance its efficacy can advantageously be made when indicated by these observations.

If labeling of the tumor is desired, generation of the fluorescent protein in tumor cells has been described by the present applicants in U.S. Pat. Nos. 6,251,384 and 6,235,968, both incorporated herein by reference. Briefly, viral vectors, preferably retroviral vectors, for expression of a fluorescent protein can be administered to subjects already harboring solid tumors. Alternatively, expression vectors may be injected intratumorally in the case of solid tumors. Model systems can be obtained by implantation into an immunocompromised or syngeneic animal of tumors which have been generated from cells modified to contain an expression system for a fluorescent protein. A variety of methods is described which result in labeling the tumor itself.

With respect to labeling the bacteria, the nucleotide sequence encoding the fluorescent protein may be introduced into the bacteria by direct modification, such as modification of the genome to locate the fluorescent protein encoding sequence in a suitable position under the control sequences endogenous to the bacteria, or may be introduced using appropriate expression vectors. The bacteria selected are bacteria that will survive and proliferate preferably selectively, if not completely specifically, in solid tumors, leaving the remainder of the host animal substantially uninhabited preferably even if the bacteria are administered systemically. Preferably the bacterial culture will be dispersed in the tumor volume as opposed to concentrated into small colonies.

The present invention provides a straightforward method to determine the most favorable bacterial hosts by direct observation in situ. Thus, the strain selected is labeled by insertion into the genome or by provision of an expression vector and administered to the animal. The pattern of proliferation in the tumor as opposed to other tissues can then be directly observed and the strain with the desired pattern chosen. A wide variety of candidates which are able to proliferate in tumors is known in the art, including *E. coli, Salmonella, Clostridium*, Lactobacilli, Bifidobacteria and the like. Suitable control sequences for expression in these systems are by now also well known in the art, or endogenous control sequences may be used.

In many cases, it may be desirable further to modify the bacteria to disable any ability to produce a toxic effect. This is more frequently the case for obligate anaerobes. If the bacteria secrete toxins, deletion or inactivation of the genes producing the toxin may be required; if the bacteria produce materials that engender undesired side effects, the genes encoding these materials may be inactivated or removed. If labeling is used, the bacteria are modified either to express the fluorescent protein under control of a constitutive promoter as a constant feature of cell growth and reproduction, or the encoding sequence may be placed in the genome at particular desired locations, replacing endogenous sequences.

In addition to exerting its own inherent antitumor affects, the bacteria may also be modified to produce a therapeutic, such as IL2 or methioninase. In one embodiment the therapeutic protein is optionally generated as a fusion protein with a fluorescent protein. If the tumor and/or the bacteria are labeled, the color of the fluorescent protein in the fusion should be a different color than that chosen in either of the other two cases. Construction of fusions with fluorescent proteins are well known as markers, as described above. The expression system for the therapeutic protein, either alone or as a fusion with fluorescent protein, can be placed on a vector or in the genome of the bacteria and the control sequences may be constitutive or, in many cases, inducible and dependent on either in situ factors or externally supplied transcription factors.

One specific preferred example of a therapeutic protein is methioninase which exerts an antitumor affect when supplied intracellularly as disclosed in PCT publication WO 00/29589, incorporated herein by reference or when supplied as a drug as described in U.S. Pat. No. 5,690,929, and in WO 94/11535 also incorporated herein by reference. The recombinant production of methioninase is also disclosed in these documents.

In addition to its inherent effect on tumors, a therapeutic protein which is an enzyme can also be used to release a toxic substance from a prodrug. For example, Miki, K., et al., *Cancer Research* (2001) 61:6805-6810 describe work which takes advantage of the toxicity of methyl selenol. This compound can be generated from selenomethionine by the action of methioninase. This article describes experiments in which the production of methyl selenol from selenomethionine by recombinantly generated methioninase kills cancer cells transformed with an expression system for this enzyme. The recombinant production of methioninase in the presence of selenomethionine can thus be used as a treatment for cancer.

In one embodiment of the invention which is provided for illustration only, bacteria such as *B. longum* or *C. novyi* are modified to disable production of any toxins. The detoxified bacteria are modified to contain an expression system for methioninase fused to a fluorescent protein. In addition, the bacteria are modified to contain an expression system for a fluorescent protein to label the bacteria per se, if desired. If the methioninase gene is constitutively expressed, this may be unnecessary as production of the methioninase itself will signal the presence of the bacteria. The thus modified bacteria are then administered to an experimental model subject harboring a tumor, such as a tumor formed from human MDA-MB-435 breast cancer cells which have been, themselves, labeled with a fluorescent label of a color other than that used in the fusion protein. Alternatively, the tumor is indigenous and labeled using a viral expression vector as described in U.S. Pat. Nos. 6,251,384 and 6,235,968 cited above.

If bacterial cells are used, the cells are injected to the tumor directly; if spores are used, intravenous injection may also be used. Direct intratumoral injection of spores is also possible. IV injection of bacteria is also possible. The appropriately modified bacteria are administered to the subject in any practical manner. While in the case of an experimental tumor model, it may be necessary for the subject to be either immunocompromised or syngeneic with the tumor in order to provide the model, the administration of the bacteria per se does not require that the subject be immunocompromised. Thus, in the case of subjects bearing indigenous tumors, immunosuppression is unnecessary. Infection in the tumor occurs readily in animals with intact immune systems. However, immunocompromised subjects may also be useful in studying the progress of the condition where the tumor is artificially introduced.

In one embodiment, the label for production of methioninase emits red fluorescence (RFP) that characteristic of the bacteria emits blue fluorescence (BFP) and that characteristic of the tumor emits green fluorescence (GFP).

In addition, if desired, selenomethionine is injected into the tumor, or systematically supplied. Production of methioninase per se and/or the presence of the bacteria per se are toxic to the tumor. The released methyl selenol is toxic not only to the immediate area in which the bacteria reside, but also diffuses more extensively to live tumor tissue. The progress of this therapy can be directly monitored by simultaneous imaging of RFP, GFP and BFP.

Fluorescent optical tumor imaging (FOTI) on whole body subjects externally permits real-time observation and monitoring of progression of infection on a continuous basis, in model systems or in subjects with indigenous tumors, and evaluation of the protocols. In subjects being treated, the availability of FOTI permits those devising treatment protocols to be informed on a continuous basis of the advisability of modifying or not modifying the protocol. Model systems are useful in the original design of treatment. In addition to external (FOTI) imaging, non-invasive endoscopic methods may also be used.

Suitable subjects for use as models are preferably mammalian subjects, most preferably convenient laboratory animals such as rabbits, rats, mice, and the like. For closer analogy to human subjects, primates could also be used. Any appropriate subject can be used, the choice being dictated mainly by convenience and similarity to the system of ultimate interest.

The following examples are offered to illustrate but not to limit the invention.

General Methods

For fluorescence dual-color imaging of bacterial-host interaction, a Leica fluorescence stereo microscope model LZ12 equipped with a mercury 50 W lamp power supply was used. To visualize both GFP and RFP fluorescence at the same time excitation was produced through a D425/60 band pass filter, 470 DCXR dichroic mirror and emitted fluorescence was collected through a long pass filter GG475 (Chroma Technology, Brattleboro, Vt.). Macroimaging was carried out in a light box (Lightools Research, Encinitas, Calif.). Fluorescence excitation of both GFP and RFP tumors was produced through an interference filter 440+/−20 nm using slit fiber optics for animal illumination. Fluorescence was observed through a 520 nm long pass filter. Images from the microscope and light box were captured on a Hamamatsu C5810 3-chip cool color CCR camera (Hamamatsu Photonics Systems, Bridgewater, N.J.). An Olympus BH 2-RFCA fluorescence microscope equipped with a mercury 100-W lamp power supply was used. To visualize both GFP and RFP fluorescence at the same time, excitation light was produced through a D425/60 band pass filter, 470 DCXR dichroic mirror. Emitted fluorescence light was collected through a long pass filter GG475 (Chroma Technology). High-resolution images of 1,024/724 pixels were captured by a Hamamatsu C5810 three-chip cooled color CCR camera (Hamamatsu Photonics) and directly stored on an IBM PC. Images were processed for contrast and brightness and analyzed with the use of IMAGE PRO PLUS 4.0 software (Media Cybernetics).

Differences among treatment groups were assessed using ANOVA using Statistica (Statsoft, Inc., Tulsa, Okla.). Kaplan-Meier analysis with a log rank test was used to determine survival. A p≤0.05 was considered to be statistically significant.

EXAMPLE 1

Preparation of S. typhimurium A1

A single clone S. typhimurium (ATCC 14028) (Stratagene, San Diego, Calif.) was picked from LB agar plate and cultured in 5 ml of liquid LB medium, shaken at 300 rpm, at 37° C. overnight. The overnight cultures were diluted 1:10 with LB medium and incubated at 37° C. The cultured bacteria were measured at $OD_{600}$ for each time point.

At mid-log phase, the cells were harvested at 4° C., washed three times with ice-cold glycerol (10% V/V) and resuspended in approximately 1/100 of the original culture volume of ice-cold glycerol (10% V/V). $2.0 \times 10^8$ cells in 40 μl were mixed with 2 μl of pGFP (Clontech) vector and placed on ice for 5 min before electroporation with a Gene Pulser apparatus (Bio-Rad Labs) according to the manufacturer: Electroporation was done at 1.8 kv setting with the pulse controller at 1,000Ω parallel resistance. One milliliter of SOC medium was added immediately after electric pulsing, and the cell suspension was transferred into a 17×100 mm polypropylene tube and incubated at 37° C. for 1 hour. Cells were spread on LB agar plates, and incubated at 37° C. overnight. Successful clones expressing GFP were designated S. typhimurium-GFP.

S. typhimurium-GFP was grown in 10 ml to the mid-log phase in LB medium. Freshly prepared nitroso-guanidine. (1 mg/ml in sterile water) was added to the washed culture to a final concentration of 100 μg/ml in TRIS-maleic acid buffer at pH 6.0. The culture was incubated at 37° C. without shaking for 30 min, then centrifuged and resuspended in an equal volume of nutrient broth medium. The cells were centrifuged again and resuspended in nutrient broth medium.

Since independent mutations were desired, the culture was divided into a number of subcultures. After the colonies reached approximately 3 mm in diameter, they were replica-plated on minimal agar and on nutrient agar plates. After the colonies have grown, those which grew on the nutrient agar, but not on the minimal agar plates were isolated as candidate auxotrophs.

The identified auxotrophic colonies were isolated with sterile toothpicks and streaked in 0.6 cm-wide patches onto fresh plates of nutrient agar, and allowed to grow at 37° C. The resulting colonies were replica-plated in supplemented M56 minimal medium agar plates containing the specific amino acids to identify the requirements of the auxotrophs.

One clone, designated A1 was identified as a Leu and Arg double auxotrophic by this analysis. The results are shown in Table 1.

TABLE 1

S. typhimurium A1 growth in minimal medium supplemented with various combinations of amino acids

| Supplemented amino acid | A1 auxotrophic mutant growth |
| --- | --- |
| Leu | No |
| Arg | No |
| All amino acids | Yes |
| All amino acids without Leu | No |
| All amino acids without Arg | No |
| Leu and Arg | Yes |

All supplements were at a final concentration of 20 μg/ml.

For growth, a single clone S. typhimurium A1 was picked from LB agar plate and cultured in 5 ml of liquid LB medium, shaken at 300 rpm, at 37° C. overnight. The overnight cultures were diluted 1:10 with LB medium and incubated at 37° C. The cultured bacteria were measured at $OD_{600}$ for each time point.

EXAMPLE 2

In Vitro Bacterial Invasion and Intracellular Replication of Tumor Cell Lines

Tumor cells were grown in 24-well tissue culture plates to a density of approximately $10^4$ cells/well. Bacteria were grown to mid-log phase, late-log phase and stationary phase ($OD_{600}$=0.3 0.6, 1.2, 2.0) in LB broth as described above. The bacteria were diluted in cell culture medium and added to the tumor cells ($1 \times 10^5$/ml) and placed in an incubator at 37° C. After 1 hour, the cells were rinsed and cultured in medium containing gentamicin sulfate (20 μg/ml) to kill external but not internal bacteria. Intracellular bacteria were observed at different time point under fluorescence microscopy.

The virulence of S. typhimurium-GFP in tumor cells is affected by the bacterial growth state: Bacteria in the mid-log phase are the least virulent and regain their invasiveness in the late-log and stationary phases. Bacteria in the late-log phase were the most virulent for killing PC-3 tumor cells. These results at 24 hours after infection are shown in FIG. 1.

The A1 auxotroph also invaded and replicated intracellularly in human PC-3 prostate cancer and mouse mammary tumor (MMT) cells in vitro and eventually induced apoptosis. The interaction between the tumor cells and bacteria was visualized by dual-color fluorescence with GFP-expressing S. typhimurium-A1 growing in RFP-expressing tumor cells, prepared as described in Example 3.

In more detail, PC-3 human prostate tumor cells and MMT mouse tumor cells, both labeled with RFP, were grown in 24-well tissue culture plates to a density of approximately $10^4$ cells/well. Bacteria were grown in LB and harvested at late-log phase, then diluted in cell culture medium and added to the tumor cells ($1 \times 10^5$ CFU/well). After 1 hour incubation at 37° C., the cells were rinsed and cultured in medium containing gentamicin sulfate (20 µg/ml) to kill external but not internal bacteria. Interaction between bacteria and tumor cells was observed at different time points under fluorescence microscopy magnification (400×).

EXAMPLE 3

Preparation of In Vivo Tumor Model

Tumors were labeled with RFP by retroviral transduction, PT67, an NIH3T3-derived packaging cell line, expressing the 10 A1 viral envelope, was purchased from CLONTECH Laboratories, Inc. PT67 cells were cultured in DME (Irvine Scientific, Santa Ana, Calif.) supplemented with 10% heat-inactivated fetal bovine serum (FBS)(Gemini Bio-products, Calabasas, Calif.). For vector production, packaging cells (PT67), at 70% confluence, were incubated with a precipitated mixture of DOTAP™ reagent (Boehringer Mannheim), and saturating amounts of pLNCX$_2$-DsRed-2-RFP plasmid for 18 hours. The host pLNCX$_2$ vector purchased from CLONTECH Laboratories, Inc. (Palo Alto, Calif.), contains the neomycin resistance gene for antibiotic selection in eukaryotic cells. The RFP gene, (DsRed2, CLONTECH Laboratories, Inc., Palo Alto, Calif.), was inserted in the pLNCX$_2$ vector at the Egl II and Not I sites. Fresh medium was replenished and the cells were examined by fluorescence microscopy 48 hours post-transfection. For selection, the cells were cultured in the presence of 500 µg/ml-2,000 µg/ml of G418 increased in a step-wise manner (Life Technologies, Grand Island, N.Y.) for seven days.

Human prostate cancer line PC-3 and mouse mammary tumor MMT060562 were cultured in RPMI (GIBCO) containing 10% fetal bovine serum (FBS)(Gemini Bio-products, Calabasas, Calif.). For expression-vector transfection, near-confluent cells were incubated with a precipitated mixture of LipofectAMINE™ plus (GIBCO), and saturating amounts of the RFP-expressing pLNCX$_2$-DsRed-2-RFP for 6 hours before being replenished with fresh medium. Cells were harvested with trypsin/EDTA 48 hours post-transfection, and subcultured at a ratio of 1:15 into selective medium which, contains 200 µg/ml of G418. Cells with stably integrated plasmids were selected by growing transiently-transfected cells in 200 µg/ml of G418-containing medium. Clones were isolated with cloning cylinders (Bel-Art Products, Pequannock, N.J.) by trypsin/EDTA and were amplified and transferred using conventional culture methods in the absence of selective agent.

Nu/nu mice, 6 weeks old, male, were used for tumor models and infection studies. In general, tumor cells ($2 \times 10^6$) labeled as described above with RFP were injected subcutaneously, RFP-labeled tumors obtained this way were administered orthotopically. All animal studies were conducted in accordance with the principles and procedures outlined in the National Institutes of Health (NIH) Guide for the Care and Use of Laboratory Animals under assurance number A3873-1.

EXAMPLE 4

Behavior of A1 In Vivo

A1 auxotrophs were grown overnight on LB medium and then diluted 1:10 in LB medium, harvested at late-log phase and washed with PBS then diluted in PBS. The A1-auxotrophs were and injected directly into the central areas of the of the RFP labeled tumors of Example 3 under fluorescence guidance, using two injection sites of 50 µl each for a total of 100 µl and $10^9$ cfu per tumor, or injected into the tail vein of nude mice with RFP orthotopic tumors ($10^7$ cfu/11001 of PBS), or injected into the peritoneum of nude mice with RFP orthotopic tumors ($10^7$ cfu/100 µl of PBS).

Under anesthesia, the animals were sacrificed. Tissue samples were obtained from lung, liver, spleen, kidney and heart and tumor. Normal tissues and tumors were excised and a sample is weighed and prepared to measure infectious bacteria by plating. For biodistribution studies, cfu of the tumors and normal mouse tissues were determined at different time points after inoculation by harvesting these tissues, homogenizing, and plating on nutrient media and counting bacterial colonies. Tissues were also prepared for standard frozen section and hematoxylin and eosin histopathological analysis according to Low, B., et al., *Nature Biotech*. (1999) 17:37-41.

In one experiment, NCR nude mice, 6-8 weeks, were implanted subcutaneously (s.c.) on the mid-right side with $2 \times 10^6$ RFP-labeled PC-3 human prostate tumor cells using a 22-gauge needle. A1 cultures were harvested at late-log phase and washed with PBS then diluted in PBS and injected directly in the center area of the tumor, using two separate sites with injections of 50 µl each, for a total of 100 µl and $10^9$ cfu per tumor. The tumor regressed over a period of 26 days.

In another experiment, using IV administration, NCR nude mice, 6-8 weeks were implanted subcutaneously (s.c.) on the mid-right side with $2 \times 10^6$ RFP-labeled PC-3 human prostate tumor cells using a 22-gauge needle. A1 auxotrophs were grown overnight on LB medium and then diluted 1:10 in LB medium, harvested at late-log phase and washed with PBS then diluted in PBS and injected into the tail vein ($10^7$ cfu/100 µl of PBS). For biodistribution studies, cfu of A1 in the tumors and normal mouse tissues were determined 5 and 10 days after tail vein injection by harvesting these tissues, homogenizing, and plating on nutrient media.

The tumor:liver bacterial ratios ranged between 500:1 to 2000:1 by day-4 after injection as shown in Table 2.

TABLE 2

Tumor and Liver Distribution of *S. typhimurium* A1

| | CFU/g tissue | | |
|---|---|---|---|
| Time post-inoculation | Tumor | Liver | Tumor:Liver |
| 5 days | $2.5 \times 10^9$ | $1 \times 10^5$ | 2500:1 |
| 10 days | $2 \times 10^{10}$ | 0 | |

A1 selectively grew in the PC-3 tumor and suppressed tumor growth after tail vein injection and after intratumor injection. After intratumor injection, the tumor completely regressed by day-20 with no obvious adverse effect on the host.

A1 also grew in the RFP-labeled MARY-X breast tumor implanted subcutaneously as described above for PC-3. Growth was progressive over time as visualized by GFP expression.

EXAMPLE 5

Comparative Toxicity of A1 and Parental Strain

A1 and the wild-type parental *S. typhimurium* were administered to non-tumor-bearing animals. The animals survived after A1 injection and died after the parental strain was injected.

Figure 2:
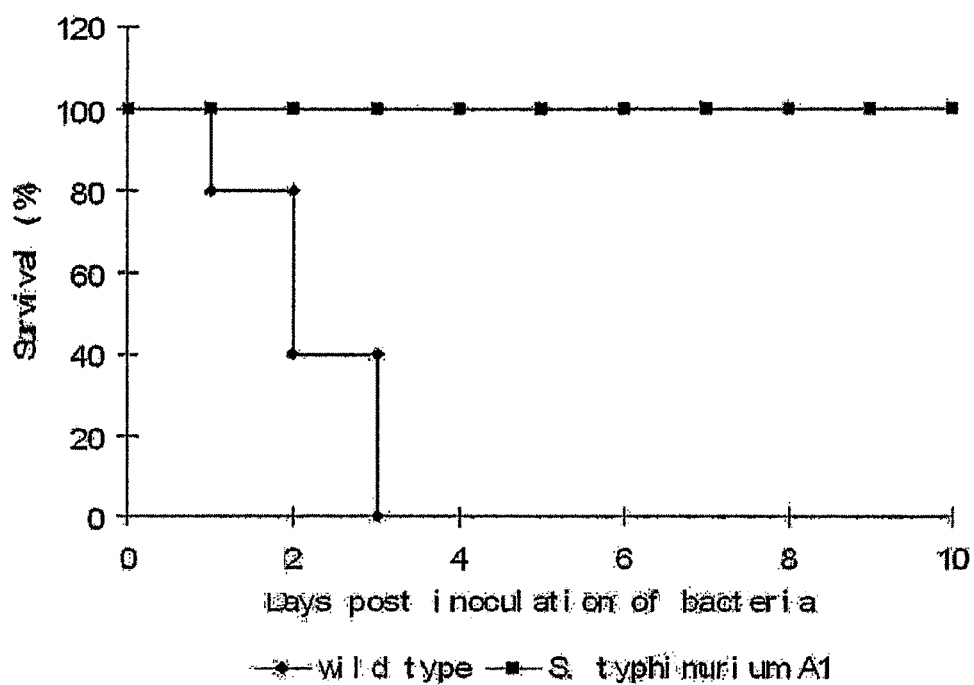
FIG. 2 is a graph comparing the toxicity of mutant A1 compared to wildtype in non-tumor-bearing nude mice.

Wildtype and A1 were grown overnight on LB medium and then diluted 1:10 in LB medium, harvested at late-log phase, washed with PBS, then diluted in PBS and injected directly into the tail vein ($10^7$ cfu/100 µl PBS). Survival of mice was determined over time after injection. n=20 animals. The results are shown in FIG. 2. As shown, A1 was substantially non-toxic, while all of the mice injected with wildtype died after three days.

Figure 3:
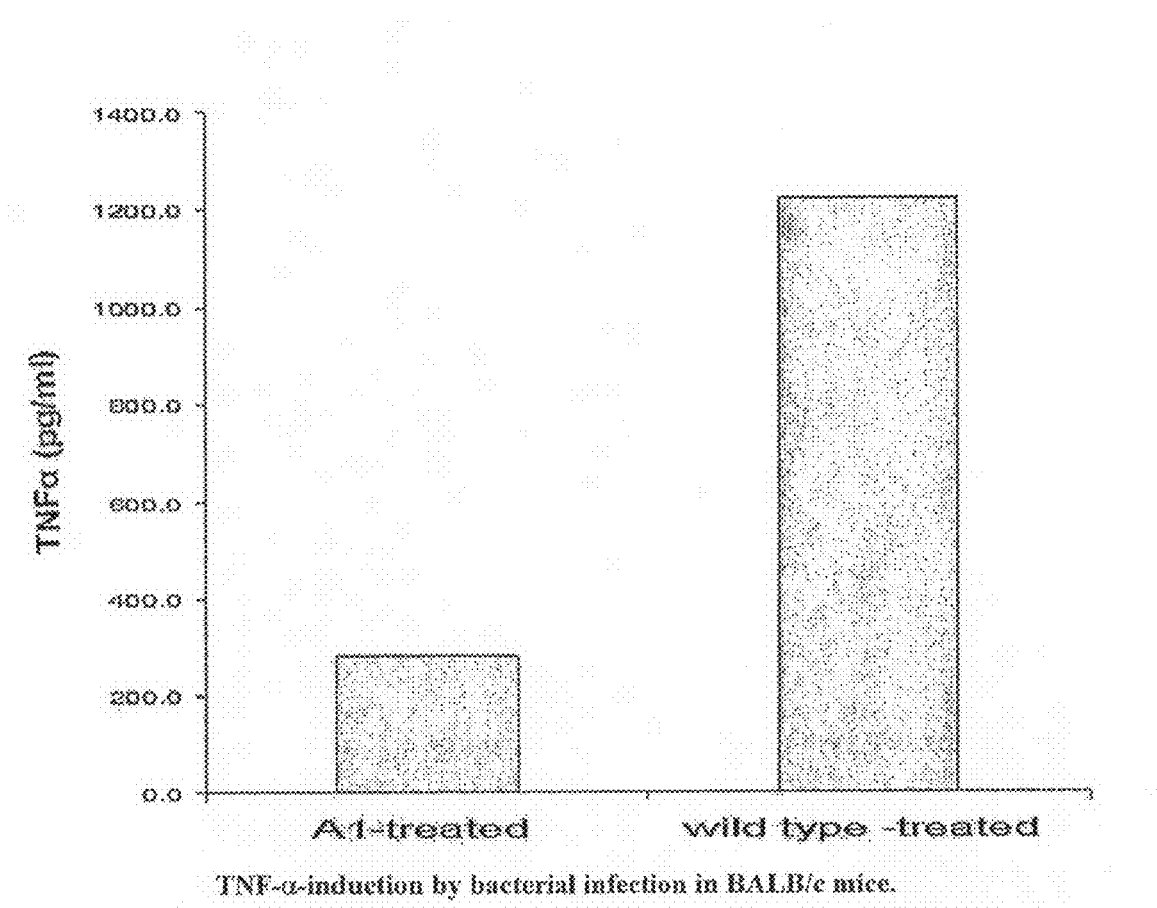
FIG. 3 compares TNFα induction by bacterial infection in BALB/c mice of the A1 mutant as compared to wildtype.

Further, A1 showed much less TNF-α induction than parental wild-type *S. typhimurium* when injected in mice. *S. typhimurium* A1, and wildtype were grown overnight on LB medium and then diluted 1:10 in LB medium, harvested at late-log phase, washed with PBS then diluted in PBS. $1\times10^6$ cfu were injected into the tail vein of female BALB/c mice (8 week n=10 animals), with PBS as a negative control. After 1.5 h, serum was collected and centrifuged to remove the cellular content. TNF-α was analyzed with a Biosource International Cytoscreen ELISA kit and results were determined with a Tecan Sunrise microplate reader. The results are shown in FIG. 3. As shown, TNFα production was greatly reduced when A1 mutants were inoculated as compared to wildtype.

*S. typhimurium* A1 disappeared from the liver by day-10; disappeared from the spleen by day-15; disappeared from the lung by day-14; and disappeared from the kidney by day-4.

EXAMPLE 6

Therapeutic Effect of A1

Figure 4:
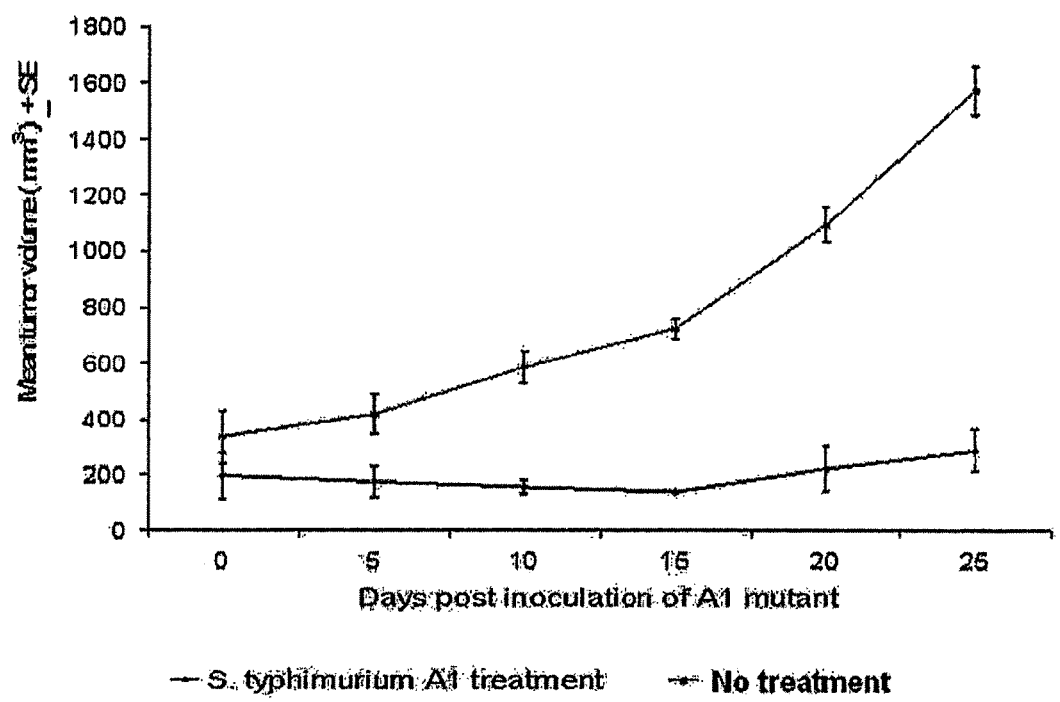
FIG. 4 is a graph showing the effect of mutant A1 on the growth of PC-3 prostate cancer in nude mice after IV injection.

NCR nude mice, 6-8 weeks, were implanted subcutaneously (s.c.) on the mid-right side with $2\times10^6$ RFP-labeled PC-3 human prostate tumor cells using a 22-gauge needle. The A1 mutants were grown overnight on LB medium and then diluted 1:10 in LB medium, harvested at late-log phase, washed with PBS, then diluted in PBS and injected directly into the tail vein ($10^7$ cfu/100 µl of PBS). Tumor size was determined from fluorescence imaging at each time-point after infection. Mean for n=10 animals. The results are shown in FIG. 4. As indicated, treatment with A1 resulted in inhibition of tumor growth, while the untreated tumor grew dramatically over a 25-day period.

Figure 5:
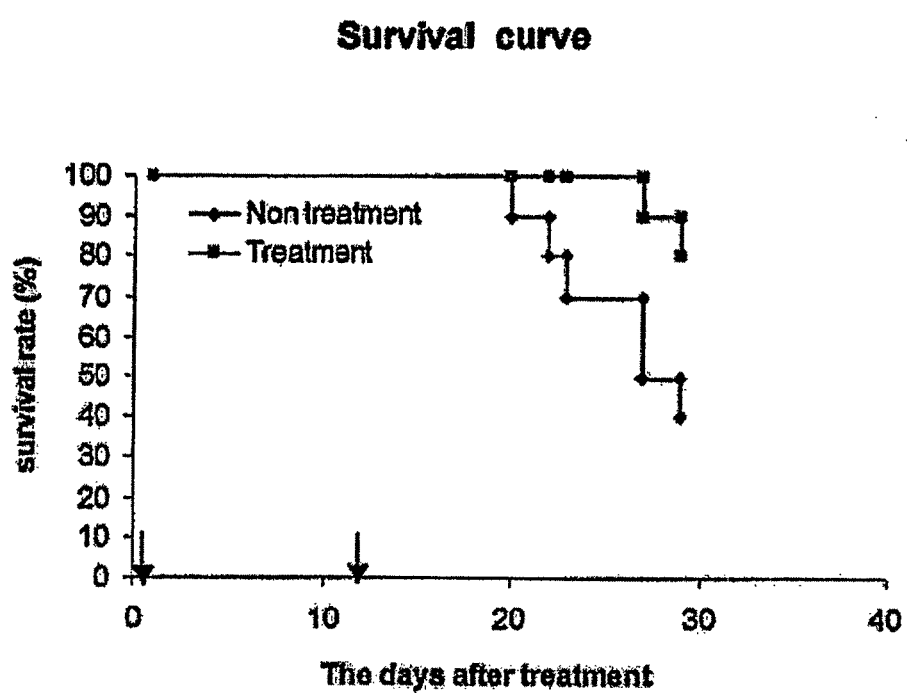
FIG. 5 is a graph showing the increased survival attainable in a PC-3 tumor model by injection of the A1 mutant.

In addition, survival time was increased in this model as shown in FIG. 5. As shown in this figure, A1 bacteria were injected at Day 0 and Day 12; the survival rate of the mice injected with A1 is 80% after 30 days, while the survival rate of controls is only 40% at that time.

EXAMPLE 7

Enhancement of Antitumor Properties Strain A2

A1 bacteria, labeled with GFP as described in Example 1, were injected into the tail vein of an HT-29 human colon tumor-bearing nude mouse. Three days after infection, the tumor tissue was removed, homogenized and diluted into PBS. After separation, the supernatant from the tumor tissue was cultured at LB agar plate at 37° C. overnight. Individual colonies were cultured and the colony with the brightest green fluorescence was picked and cultured into 5 ml of LB medium. The resolved strain, designated A2, remained auxotrophic for Arg and Leu.

To test A2 for adherence to tumor cells, RFP-labeled HT-29 human breast cancer cells were grown in 24-well tissue culture plates to a density of approximately $10^4$ cells/well. A2 isolates were grown to late-log phase in LB broth, diluted in cell culture medium ($1\times10^6$), added to the tumor cells and placed in an incubator at 37° C. After 60 min, the cells were rinsed five times with 1-2 ml of PBS. Adherent bacteria were released by incubation with 0.2 ml of 0.1% Triton X-100 for 10 min. LB broth (0.8 ml) was then added and each sample was vigorously mixed using a pipet. Adherent bacteria were quantitated by plating for cfu on LB agar medium.

This quantitative assay showed that the quantity of A2 auxotrophs attached to HT-29 tumor cells was about six times higher than the number of A1 auxotrophs.

To measure invasiveness, the rinsed cells were cultured in medium containing gentamycin sulfate (20 µg/ml) to kill external, but not internal, bacteria. After incubation with the gentamicin for 12 hours, the cells were washed once with PBS, and the viable intracellular bacteria were evaluated by fluorescence microscopy.

A2 isolates had a greater capacity to enter and grow into the HT-29 tumor cells. About 20% of tumor cells were invaded by A1 bacteria, but about 80% of the tumor cells were invaded by A2 bacteria.

To text virulence, dual-color labeled PC-3 human prostate tumor cells were grown in 24-well tissue culture plates to a density of approximately $10^4$ cells/well. Bacteria were grown to late-log phase in LB broth as described above. The bacteria were diluted in cell culture medium ($1\times10^6$), added to the tumor cells and placed in an incubator at 37° C. After 30 min, the cells were rinsed and cultured in medium containing gentamycin sulfate (20 µg/ml) to kill external but not internal bacteria. Virulence was observed under fluorescence microscopy at different time points.

A2 bacteria showed strong virulence in PC-3 tumor cells which started dying one hour after infection. Three hours after infection, 95% of the cells were killed completely from apoptosis and necrosis. In a previous study using A1 bacteria, cell death began to occur only after about 12 hours.

Thus, A1 *S. typhimurium* auxotrophs passaged into the HT-29 colon tumor mouse model underwent physiological or genetic changes which resulted in enhanced antitumor properties, including enhanced adherence, invasiveness, and virulence. Attempts to modify the A1 strain by passage through the PC-3 and Mary-X tumor models, however, did not result in strains showing these modified properties.

EXAMPLE 8

Behavior of A2 In Vivo

The GFP labeled A2 bacteria were injected into the tail vein of nude mice PC-3 tumor models at $10^7$ cfu/100 µl of PBS. The tumor model is prepared as in Example 4.

In the PC-3 model, all treated mice showed tumor damage after injection of the A2 bacteria and two of five animals became tumor free after 20 days. Their survival times were comparable to those of healthy mice.

Paraffin sections of the infected PC-3 tumor from the injected mice showed that A2 invaded and damaged the tumor. As described above, only intratumor injection of A1 resulted in complete tumor removal.

Similar results were obtained in a model using Mary-X human breast tumor cells labeled with RFP. All five treated animals showed destruction of the tumor and tumor regression. In three of the five treated animals, the tumor was completely removed and there was no obvious adverse effect on the host.

The distribution of A2 bacteria was evaluated using the microscopic technique described above and it was shown to be widely distributed in the tumor. A2 did not appear toxic to the host. Normal tissue, such as liver and spleen, were infected by labeled A2 after injection, but A2 completely disappeared from normal tissue over time.

The invention claimed is:

1. A culture comprising a *Salmonella typhimurium* mutant which is auxotrophic only for arginine and leucine, prepared by exposing wildtype *S. typhimurium* to random mutations and testing individual colonies for amino acid requirements, followed by passaging said auxotrophs through an in vivo animal tumor model and recovering colonies of said mutant from tumor tissue of said animal model.

2. A pharmaceutical or veterinary composition which comprises the *S. typhimurium* mutant of claim 1.

3. The culture of claim 1, wherein said *S. typhimurium* mutants are further modified to produce a therapeutic protein.

4. The culture of claim 3, wherein the therapeutic protein is IL2 or methioninase.

5. A pharmaceutical or veterinary composition comprising the culture of claim 3.

6. The culture of claim 1, wherein the *S. typhimurium* mutants are further modified to produce a fluorescent protein.

7. The culture of claim 6, wherein the fluorescent protein is a green fluorescent protein (GFP).

8. A pharmaceutical or veterinary composition comprising the culture of claim 6.

9. The culture of claim 1 wherein said auxotrophs are labeled with a fluorescent protein when subjected to the step of passaging said auxotrophs through an in vivo animal tumor model and recovering colonies from said tumor tissue.

* * * * *